US012793833B2

(12) United States Patent
Turchenko et al.

(10) Patent No.: US 12,793,833 B2
(45) Date of Patent: Nov. 10, 2026

(54) SYSTEM AND METHOD FOR CONTACTLESS PREDICTIONS OF VITAL SIGNS, HEALTH RISKS, CARDIOVASCULAR DISEASE RISK AND HYDRATION FROM RAW VIDEOS

(71) Applicant: NURALOGIX CORPORATION, Toronto (CA)

(72) Inventors: Volodymyr Turchenko, Burlington (CA); Naresh Vempala, Pickering (CA); Marzio Pozzuoli, King (CA); Winston De Armas, Hamilton (CA); Hassan Nikoo, Richmond Hill (CA); Pei Ding, North Vancouver (CA); Pu Zheng, Toronto (CA); Seyed Reza Mousavi, Markham (CA); Evgueni Kabakov, North York (CA)

(73) Assignee: NURALOGIX CORPORATION, Toronto (CA)

( * ) Notice: Subject to any disclaimer, the term of this patent is extended or adjusted under 35 U.S.C. 154(b) by 93 days.

(21) Appl. No.: 18/840,243

(22) PCT Filed: Mar. 23, 2023

(86) PCT No.: PCT/CA2023/050386
§ 371 (c)(1),
(2) Date: Aug. 21, 2024

(87) PCT Pub. No.: WO2023/178437
PCT Pub. Date: Sep. 28, 2023

(65) Prior Publication Data

US 2025/0185924 A1 Jun. 12, 2025

Related U.S. Application Data

(60) Provisional application No. 63/269,902, filed on Mar. 25, 2022.

(51) Int. Cl.
*G16H 30/00* (2018.01)
*A61B 5/00* (2006.01)
(Continued)

(52) U.S. Cl.
CPC .......... *G16H 30/00* (2018.01); *A61B 5/0077* (2013.01); *A61B 5/02055* (2013.01);
(Continued)

(58) Field of Classification Search
CPC . A61B 5/02055; A61B 5/0077; A61B 5/7267; A61B 5/7275; G06N 20/20;
(Continued)

(56) References Cited

U.S. PATENT DOCUMENTS 11,227,161 B1 * 1/2022 Tao ........................ G06V 20/41
11,633,103 B1 4/2023 Nudd et al.
(Continued)

FOREIGN PATENT DOCUMENTS

KR 20220113298 A 8/2022
WO 2017139895 A1 8/2017
(Continued)

OTHER PUBLICATIONS

Viscaino et al., "Computer-Aided Ear Diagnosis System Based on CNN-LSTM Hybrid Learning Framework for Video Otoscopy Examination," IEEE Access, vol. 9, 2021, Digital Object Identifier 10.1109/ACCESS.2021.3132133. (Year: 2021).*
(Continued)

*Primary Examiner* — Jonathon A. Szumny
(74) *Attorney, Agent, or Firm* — Marc Lampert; Bhole IP Law

(57) ABSTRACT

A system and method for contactless predictions of one of vital signs, health risk for a disease or condition, blood biomarker values, and hydration status, the method executed on one or more processors, the method including: receiving
(Continued)

a raw video capturing a human subject; determining one of vital signs, health risk for a disease or condition, blood biomarker values, and hydration status using a trained machine learning model, the machine learning model taking the raw video as input, the machine learning model trained using a plurality of training videos where ground truth values for the vital signs, the health risk for a disease or condition, the blood biomarker values, or the hydration status were known during the capturing of the training video; and outputting the predicted vital signs, health risk for a disease or condition, blood biomarker values, or hydration status.

14 Claims, 13 Drawing Sheets

(51) Int. Cl.
*A61B 5/0205* (2006.01)
*G06N 3/045* (2023.01)
*G06N 3/0464* (2023.01)
*G06N 20/20* (2019.01)

(52) U.S. Cl.
CPC ........... *A61B 5/7267* (2013.01); *G06N 3/045* (2023.01); *G06N 3/0464* (2023.01); *G06N 20/20* (2019.01)

(58) Field of Classification Search
CPC ...... G06N 3/045; G06N 3/0464; G16H 30/20; G16H 50/20; G16H 50/30; G16H 30/00
See application file for complete search history.

(56) References Cited

U.S. PATENT DOCUMENTS

| | | | | |
|---|---|---|---|---|
| 11,864,944 | B2 * | 1/2024 | Fornwalt | A61B 8/04 |
| 11,904,224 | B2 * | 2/2024 | Atallah | G16H 40/67 |
| 2019/0031192 | A1 | 1/2019 | Mcnew | |
| 2019/0341152 | A1 | 11/2019 | Mellem et al. | |
| 2019/0385711 | A1 | 12/2019 | Shriberg et al. | |
| 2020/0237452 | A1 | 7/2020 | Wolf et al. | |
| 2020/0349702 | A1 * | 11/2020 | Kim | G16H 30/40 |
| 2020/0364868 | A1 * | 11/2020 | Zhang | G06T 7/248 |
| 2021/0106288 | A1 | 4/2021 | Howard | |
| 2021/0125732 | A1 * | 4/2021 | Patel | G06N 3/096 |
| 2021/0145404 | A1 * | 5/2021 | Fornwalt | G16H 30/20 |
| 2021/0232915 | A1 * | 7/2021 | Dalli | G06N 3/045 |
| 2021/0304001 | A1 * | 9/2021 | Po | G06N 3/0464 |
| 2021/0327562 | A1 * | 10/2021 | Kushwah | G06T 7/0016 |
| 2021/0398337 | A1 * | 12/2021 | Mcduff | G06T 13/40 |
| 2022/0093276 | A1 * | 3/2022 | Patel | G16H 40/63 |
| 2022/0240789 | A1 * | 8/2022 | Sharma | A61B 5/7253 |
| 2022/0245811 | A1 * | 8/2022 | DiGiore | G06T 7/0012 |
| 2022/0246307 | A1 * | 8/2022 | Nakamura | G16H 50/30 |
| 2022/0280028 | A1 * | 9/2022 | Moretti | A61B 1/32 |
| 2023/0032332 | A1 * | 2/2023 | Whitehill | A61B 5/746 |
| 2026/0033788 | A1 * | 2/2026 | Speth | A61B 5/02416 |

FOREIGN PATENT DOCUMENTS

| | | | | | |
|---|---|---|---|---|---|
| WO | 2019079475 | A1 | | 4/2019 | |
| WO | WO-2022224524 | A1 | * | 10/2022 | G16H 40/67 |

OTHER PUBLICATIONS

Cheng et al., "Deep Learning Methods for Remote Heart Rate Measurement: A Review and Future Research Agenda," Sensors 2021, 21, 6296. https://doi.org/; 10.3390/s21186296. (Year: 2021).*

Lazo et al., "Using spatial-temporal ensembles of convolutional neural networks for lumen segmentation in ureteroscopy," International Journal of Computer Assisted Radiology and Surgery (2021) 16:915-922; https://doi.org/10.1007/s11548-021-02376-3. (Year: 2021).*

International Search Report for PCT application No. PCT/CA2023/050386, CIPO, search completed: May 26, 2023, mailed: Jun. 22, 2023.

Written Opinion of the International Searching Authority for PCT application No. PCT/CA2023/050386, CIPO, opinion completed: Jun. 22, 2023, mailed: Jun. 22, 2023.

Ali, Sharib , et al., "A deep learning framework for quality assessment and restoration in video endoscopy.", Medical image analysis 68 (2021): 101900. https://www.sciencedirect.com/science/article/pii/S1361841520302644.

Kolosov, Dimitrios , et al., "Contactless Camera-Based Heart Rate and Respiratory Rate Monitoring Using AI on Hardware", Sensors 23.9 (2023): 4550. Retrieved from: https://www.ncbi.nhn.nih.gov/pmc/articles/PMC10181491/pdf/sensors-23-04550.pdf.

Qiu, Ying , et al., "EVM-CNN: Real-time contactless heart rate estimation from facial video", IEEE transactions on multimedia 21.7 (2018): 1778-1787. Retrieved from: https://ieeexplore.ieee.org/stamp/stamp.isp?tp=&arnumber=8552438.

Ulloa Cerna, Alvaro E. , et al., "Deep-learning-assisted analysis of echocardiographic videos improves predictions of all-cause mortality", Nature Biomedical Engineering 5.6 (2021): 546-554.

Vatanparvar, Korosh , et al., "Respiration Rate Estimation from Remote PPG via Camera in Presence of Non-Voluntary Artifacts", 2022 IEEE-EMBS International Conference on Wearable and Implantable Body Sensor Networks (BSN). IEEE, 2022. Retrieved from: https://ieeexplore.ieee.org/stamp/stamp.isp?tp=&arnumber=9928485.

Zhu, Li , et al., "Contactless SpO 2 Detection from Face Using Consumer Camera", 2022 IEEE-EMBS International Conference on Wearable and Implantable Body Sensor Networks (BSN). IEEE, 2022. Retrieved from: https://ieeexplore.ieee.org/stamp/stamp.isp?tp=&arnumber=9928509.

* cited by examiner

SYSTEM AND METHOD FOR CONTACTLESS PREDICTIONS OF VITAL SIGNS, HEALTH RISKS, CARDIOVASCULAR DISEASE RISK AND HYDRATION FROM RAW VIDEOS

TECHNICAL FIELD

The following relates generally to prediction of human conditions and more specifically to a system and method for contactless predictions of vital signs, risk of health conditions, risk of cardiovascular disease, and hydration, from raw videos.

BACKGROUND

Measurement of vital signs, such as body temperature, pulse rate, respiration rate, blood pressure are the primary approach used to diagnose various human conditions. Early diagnosis of various conditions can improve the quality and length of life of many patients. However, many current approaches for vital sign determination are either invasive, prohibitively expensive, requiring expensive bespoke machinery, require professional determination, or the like.

SUMMARY

In an aspect, there is provided a method for contactless predictions of one of vital signs, health risk for a disease or condition, blood biomarker values, and hydration status, the method executed on one or more processors, the method comprising: receiving a raw video capturing a human subject; determining one of vital signs, health risk for a disease or condition, blood biomarker values, and hydration status using a trained machine learning model, the machine learning model taking the raw video as input, the machine learning model trained using a plurality of training videos where ground truth values for the vital signs, the health risk for a disease or condition, the blood biomarker values, or the hydration status were known during the capturing of the training video; and outputting the predicted vital signs, health risk for a disease or condition, blood biomarker values, or hydration status.

In a particular case of the method, the trained machine learning model comprises a convolutional neural network.

In another case of the method, the trained machine learning model comprises an ensemble of machine learning models, the ensemble comprising the convolutional neural network and a deep learning artificial neural network.

In yet another case of the method, the deep learning artificial neural network receives features extracted by early convolution layers of the convolutional neural network as input to the deep learning artificial neural network.

In yet another case of the method, the deep learning model comprises an XGBoost model.

In yet another case of the method, the prediction for the health risk for the disease or condition comprises predicting a risk for cardiovascular disease.

In yet another case of the method, the machine learning model is trained using labeled ground truth data, the ground truth determined using a pooled cohort equation of cardiovascular disease risk.

In yet another case of the method, the prediction for health risk for the disease or condition is represented as a percentage likelihood of having the disease or condition in the future.

In yet another case of the method, the percentage likelihood for having the disease or condition is for a given timeframe in the future.

In yet another case of the method, the raw video is compressed prior to being taken as input in the machine learning model.

In another aspect, there is provided a system for contactless predictions of one of vital signs, health risk for a disease or condition, blood biomarker values, and hydration status, the system comprising one or more processors and a data storage, the data storage comprising instructions to execute, on the one or more processors: an input module to receive a raw video capturing a human subject; a machine learning module to determine one of vital signs, health risk for a disease or condition, blood biomarker values, and hydration status using a trained machine learning model, the machine learning model taking the raw video as input, the machine learning model trained using a plurality of training videos where ground truth values for the vital signs, the health risk for a disease or condition, the blood biomarker values, or the hydration status were known during the capturing of the training video; and an output module to output the predicted vital signs, health risk for a disease or condition, blood biomarker values, or hydration status.

In a particular case of the system, the trained machine learning model comprises a convolutional neural network.

In another case of the system, the trained machine learning model comprises an ensemble of machine learning models, the ensemble comprising the convolutional neural network and a deep learning artificial neural network.

In yet another case of the system, the deep learning artificial neural network receives features extracted by early convolution layers of the convolutional neural network as input to the deep learning artificial neural network.

In yet another case of the system, the deep learning model comprises an XGBoost model.

In yet another case of the system, the prediction for the health risk for the disease or condition comprises predicting a risk for cardiovascular disease.

In yet another case of the system, the machine learning module trains the machine learning model using labeled ground truth data, the ground truth determined using a pooled cohort equation of cardiovascular disease risk.

In yet another case of the system, the prediction for health risk for the disease or condition is represented as a percentage likelihood of having the disease or condition in the future.

In yet another case of the system, the percentage likelihood for having the disease or condition is for a given timeframe in the future.

In yet another case of the system, the system further comprising a preprocessing module to compress the raw video prior to being taken as input in the machine learning model.

These and other aspects are contemplated and described herein. It will be appreciated that the foregoing summary sets out representative aspects of systems and methods to assist skilled readers in understanding the following detailed description.

BRIEF DESCRIPTION OF THE DRAWINGS

The features of the invention will become more apparent in the following detailed description in which reference is made to the appended drawings wherein.

DETAILED DESCRIPTION

Figure 1:
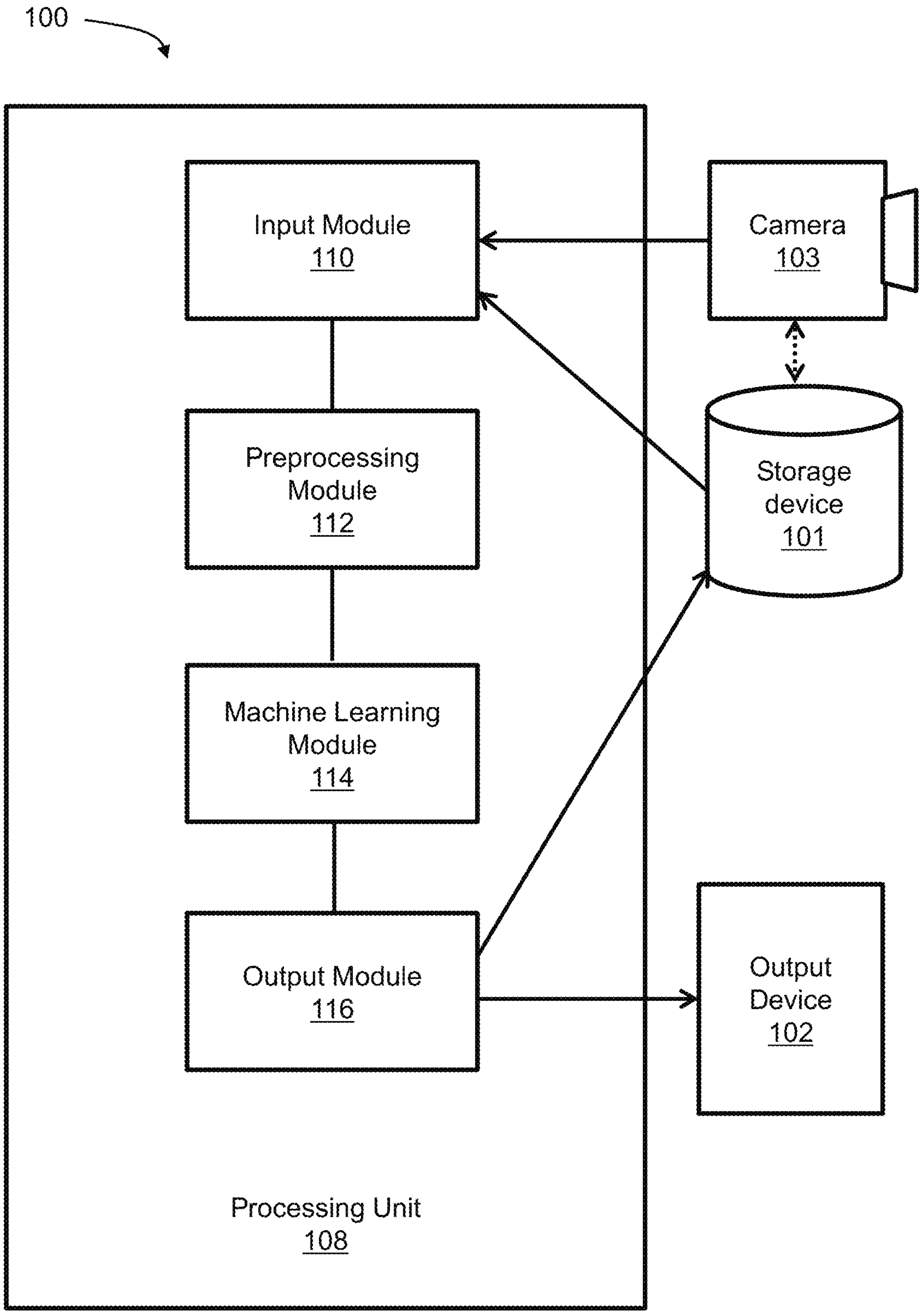
FIG. 1 is a block diagram of a system for contactless predictions of vital signs from raw videos, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to prediction of human conditions and more specifically to a system and method for contactless predictions of vital signs, risk of fatty liver disease, and hydration, from raw videos.

In embodiments of the system and method described herein, technical approaches are provided to solve the technological problem of determining human vital signs and various human conditions without having to contact a human subject by the measurement equipment. The vital signs and conditions are determined using image processing techniques performed over a plurality of images (such as those forming a video).

The technical approaches described herein offer the substantial advantages of not requiring direct physical contact between a subject and measurement equipment. As an example of a substantial advantage using the technical approaches described herein, vital sign determination can be performed on a subject using a suitable imaging device, such as by a video camera communicating over a communications channel, or using previously recorded video material.

The technical approaches described herein advantageously utilize body specific data driven machine-trained models that are executed against an incoming video stream. In some cases, the incoming video stream are a series of images of the subject's facial area. In other cases, the incoming video stream can be a series of images of any body extremity with exposed vascular surface area; for example, the subject's palm. In most cases, each captured body extremity requires separately trained models. For the purposes of the following disclosure, reference will be made to capturing the subject's face with the camera; however, it will be noted that other areas can be used with the techniques described herein.

Referring now to FIG. 1, a system for contactless predictions of vital signs from raw videos using machine learning models 100 is shown. The system 100 includes a processing unit 108, one or more video-cameras 103, a storage device 101, and an output device 102. The processing unit 108 may be communicatively linked to the storage device 101, which may be preloaded, periodically loaded, and/or continuously loaded with video imaging data obtained from one or more video-cameras 103. The processing unit 108 includes various interconnected elements and modules, including an input module 110, a preprocessing module 112, a machine learning module 114, and an output module 116. In further embodiments, one or more of the modules can be executed on separate processing units or devices, including the video-camera 103 or output device 102. In further embodiments, some of the features of the modules may be combined or run on other modules as required.

In some cases, the processing unit 108 can be located on a computing device that is remote from the one or more video-cameras 103 and/or the output device 102, and linked over an appropriate networking architecture; for example, a local-area network (LAN), a wide-area network (WAN), the Internet, or the like. In some cases, the processing unit 108 can be executed on a centralized computer server, such as in off-line batch processing.

The term “video”, as used herein, can include sets of still images. Thus, “video camera” can include a camera that captures a sequence of still images and “imaging camera” can include a camera that captures a series of images representing a video stream.

Figure 2:
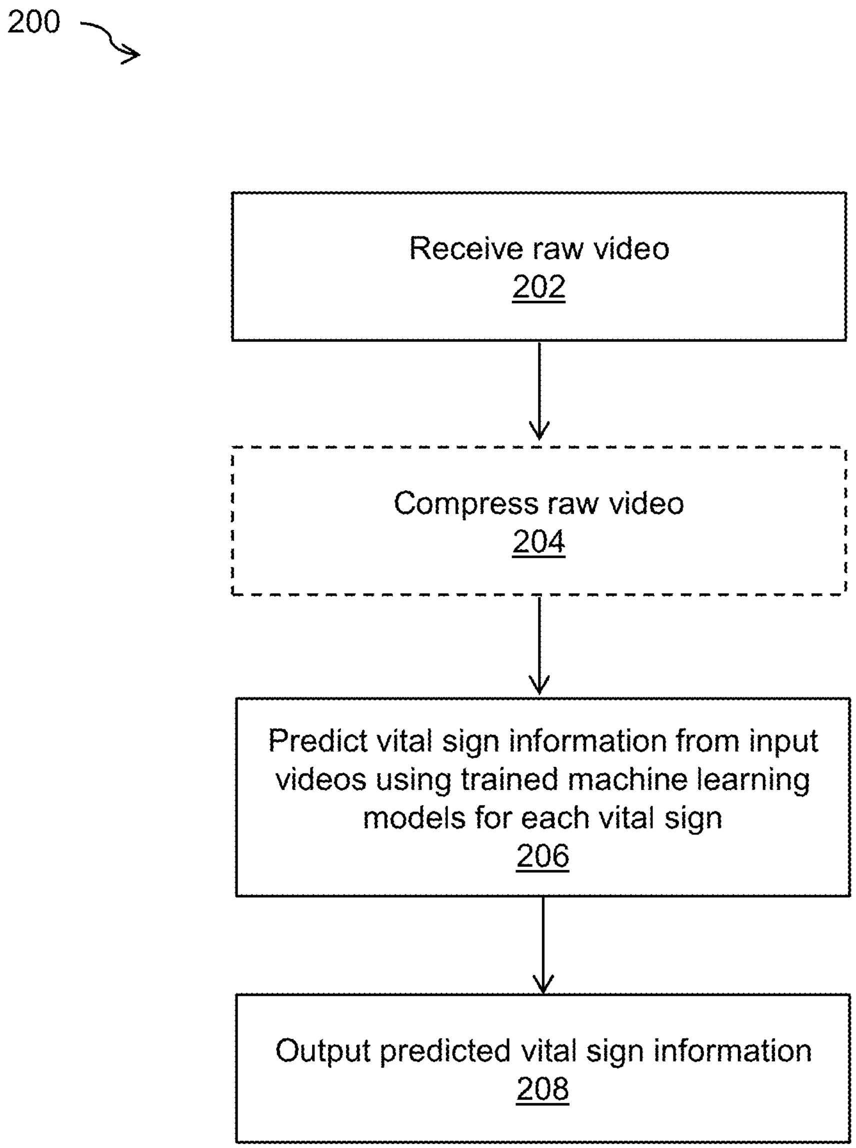
FIG. 2 is a flowchart for a method for contactless predictions of vital signs from raw videos, according to an embodiment.
Figure 5:
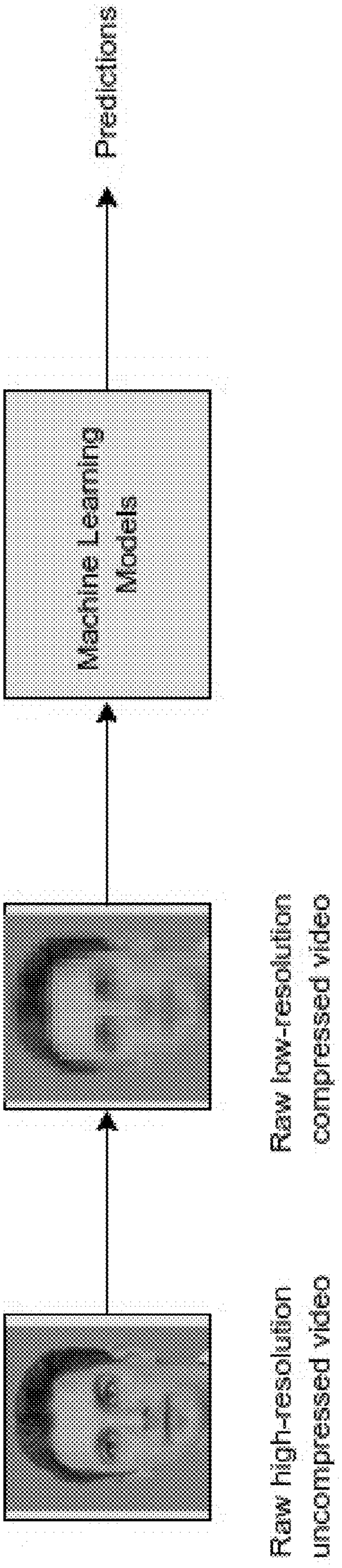
FIG. 5 is an example diagrammatic overview of the method of FIG. 2.

Turning to FIG. 2, a flowchart for a method for contactless predictions of vital signs from raw videos using machine learning models 200 is shown. Advantageously, the method 200 does not require any expert-driven manual signal processing or feature engineering. A diagrammatic overview of the method 200 is illustrated in the example of FIG. 5.

At block 202, the input module 110 receives raw video from the camera 103 and/or the storage device 101. Generally, this input raw video will be relatively high-resolution, uncompressed video.

Generally, each raw uncompressed video has been collected for a specific duration, at a specific sampling rate, and may be visualized as a series of two-dimensional frames in time, with each frame having fixed height and fixed width. In an example, each video is 30 seconds long and is collected at a sampling rate of 30 frames per second (fps), resulting in a total of 900 frames. Each frame is an image at a particular point in time, with a bit depth of, for example, 8 bits, consisting of red, green, and blue (R,G,B) color channels. In this example, each frame has a height of 1280 pixels and a width of 720 pixels and each video has an approximate size of 2.3 GB.

At block 204, in some cases, the preprocessing module 112 compresses the raw uncompressed videos to lower resolution videos. Compression enables considerable decrease in video size without any significant loss of information content that might affect accuracy of predictions. There are at least two advantages of using compressed videos. Firstly, reduced video size improves speed and ease of processing by saving memory resources and communication bandwidth. Secondly, converting to low resolution helps in anonymizing the identity of the person captured in the input video images and helps address various privacy concerns.

In an example, each raw video can be converted to a lower resolution compressed video by decreasing the height and width of each individual frame. In the above example, each video still consists of 900 frames where each frame still consists of RGB channels; however, bit depth is increased to 12 bits, height is reduced to 32 pixels, and width is reduced to 16 pixels. This results in each video having a reduced size of approximately 2.0 MB from an original size of 2.3 GB. The present inventors have conducted experiments to verify that such compression does not result in loss of information that is required for making predictions.

Figure 3:
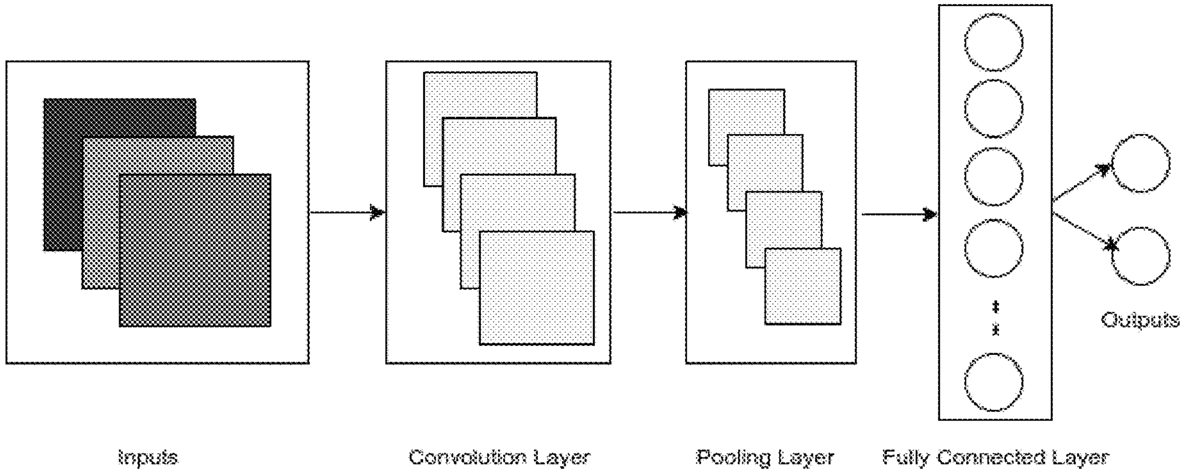
FIG. 3 illustrates a diagram of an example convolutional neural network (CNN)
Figure 4:
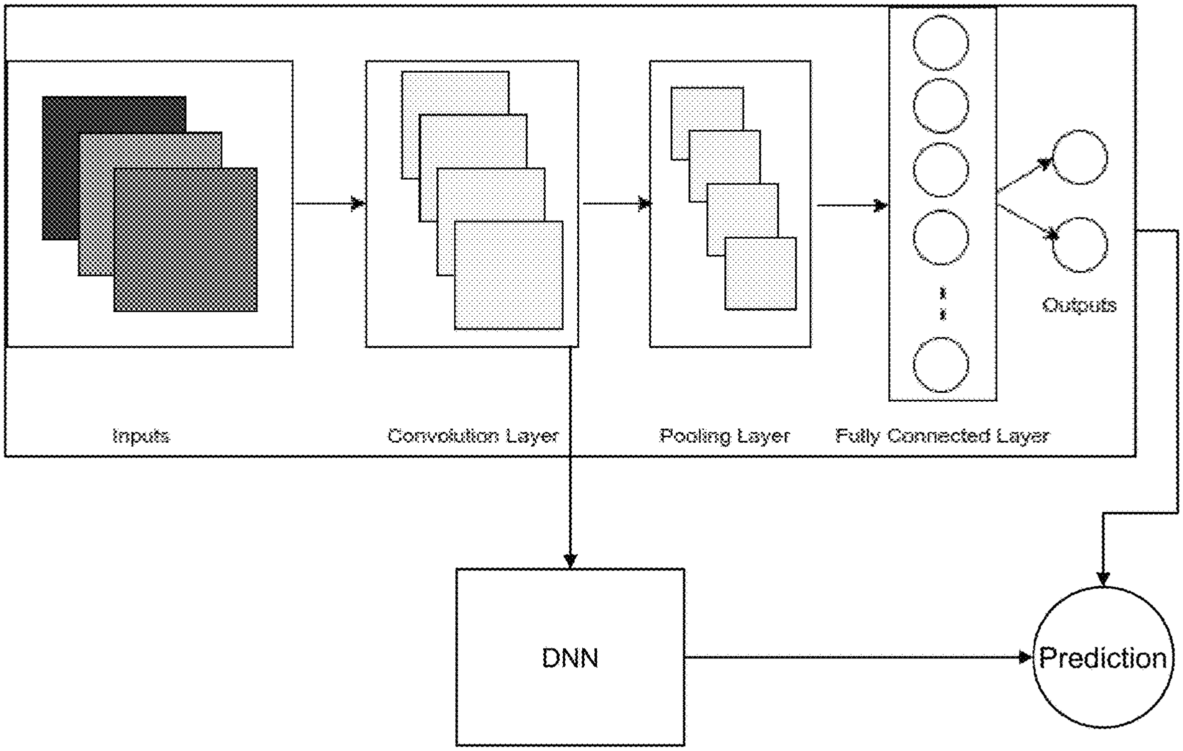
FIG. 4 illustrates a diagram of an example ensemble network.

At block 206, the machine learning module 114 feeds the compressed, or in other cases, uncompressed, videos as input to machine learning (ML) models in order to output predicted vital sign information. ML models can use any suitable approach. For example, deep learning (DL) models such as convolutional neural networks (CNNs) that is illustrated in the diagram of FIG. 3. In other cases, a trained ensemble of deep DL models can be used, including CNNs and deep neural networks (DNNs), such as multi-layer perceptrons (MLPs), that is illustrated in the diagram of FIG. 4. In some cases, the architecture of the ML model and/or ensemble can change depending on the specific vital sign to be predicted. Each vital sign will typically require a different non-linear function for prediction, thereby demanding varying levels of complexity in the model's architecture that need to be determined when training (e.g. more layers in the CNN and/or DNN, additional skipped connections in the CNN, or the like). The models can be trained using supervised learning, where each input video has a labeled set of ground truths corresponding to the vitals that are to be predicted. Models can be trained on numerous training videos; for example, thousands of videos. After training, models can be validated for their accuracy and generalizability using a combination of approaches that include k-fold cross validation, performance tuning on separated validation sets, and final performance checks on pristine test sets that represent field data. Advantageously, an ML model can be trained for each type of vital sign, allowing a single video can produce multiple vital signs by inputting such video into each respective ML model.

In a particular case, a CNN model can be used that is a three dimensional model, which receives raw compressed video input in the form of three dimensional data arrays consisting of pixel values. The CNN architecture consists of a series of convolution and pooling layers followed by a fully connected layer. The convolution layer extracts relevant features from each image frame of the video using several kernels (i.e., filters). The number of features extracted will depend on the number of filters used by the CNN. The pooling layer enables selection of the most salient features while also reducing feature dimensionality. Several of these convolution and pooling layers can be used in sequence within the architecture before finally outputting to a fully connected layer as a flattened vector. The series of convolution layers essentially provide an automated feature extraction hierarchy. For instance, early convolution layers in the CNN represent extraction of finer grained or lower-level features while convolution layers occurring later represent coarser or higher-level features.

Outputs from the fully connected layer can be adapted into either a set of class probabilities in the case of a classifier or a single prediction in the case of a regressor. Various parameters and hyperparameters can be determined during the training phase of the model, allowing customization of a model (e.g., CNN) for each vital sign, and making the model unique for determining a specific type of vital sign. Parameters and hyperparameters of the model determined during a training phase can include number of layers, choice of activation functions, number of filters, type of padding used, pooling strategy, choice of cost function, number of epochs for determining early stopping, choice of using dropout, and the like.

In some cases, depending on, for example, how complex the non-linear solution needs to be for a vital sign, an ensemble ML model can be used instead of a single model. Advantageously, this can improve the accuracy of predictions at the expense of computational cost. In an example, the ensemble can include at least two models: a CNN model and a DNN model. The DNN (or MLP) model consists of an input layer and a series of hidden layers followed by an output layer. The DNN model uses features extracted by the early convolution layers of the CNN as inputs to its network. Hyperparameters determined during a training phase can include number of input features, number of hidden layers, dimensionality of each hidden layer, activation functions used, early stopping criteria, choice of using dropout, and the like.

The machine learning module 114 determines a weight of each model's contribution. Depending on the number and types of individual ML models used (e.g. CNN, DNN, etc.), and their accuracy in making predictions on a validation set, contribution weights for each model are tuned using other ML techniques, such as linear regression with regularization.

At block 208, the output module 116 outputs the vital sign information predicted by the machine learning module 114 to the output device 102 and/or the storage device 101.

The machine trained models, described herein, use training examples that comprise inputs comprising images from videos captured of human body parts and known outputs (ground truths) of vital sign values. The known ground truth values can be captured using any suitable device/approach; for example, body temperature thermometer, a pulse oximeter, a plethysmography sensor, a sphygmomanometer, or the like. The relationship being approximated by the machine learning model is pixel data from the video images to vital sign estimates; whereby this relationship is generally complex and multi-dimensional. Through machine learning training, such a relationship can be outputted as vectors of weights and/or coefficients. The trained machine learning model being capable of using such vectors for approximating the input and output relationship between the video images input data and the predicted vital sign information. In this way, advantageously, the ML models take the multitude of training sample videos, and corresponding ground truth of vital sign values, and learn which features of input videos are correlated with which vital signs. Thus, the machine learning module 114 creates an ML model that can predict vital signs given a raw video of a person, such as a video of their face, as input.

Figure 6:
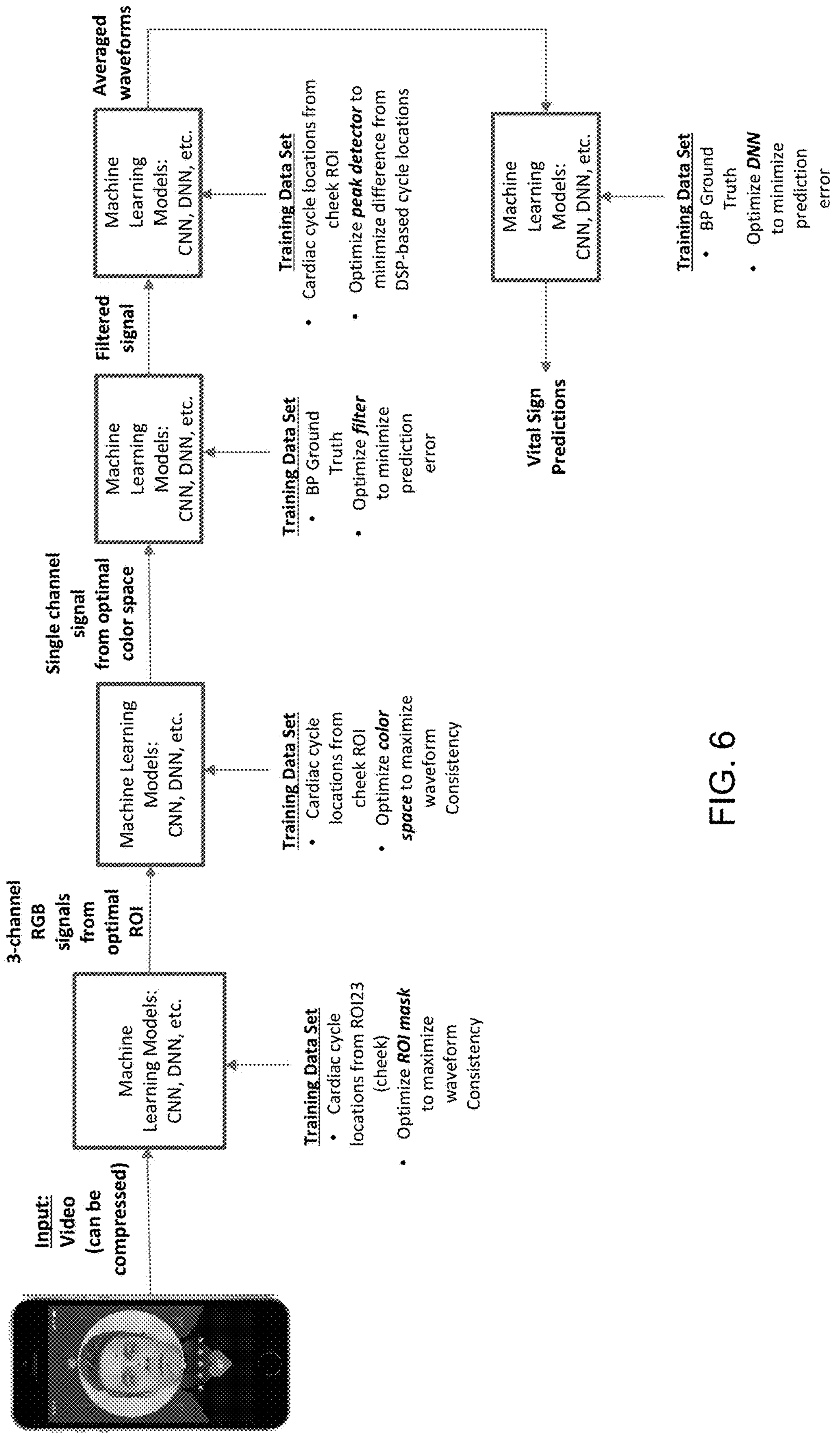
FIG. 6 is a diagram illustrating an example approach for contactless predictions of vital signs from raw videos.
Figure 7:
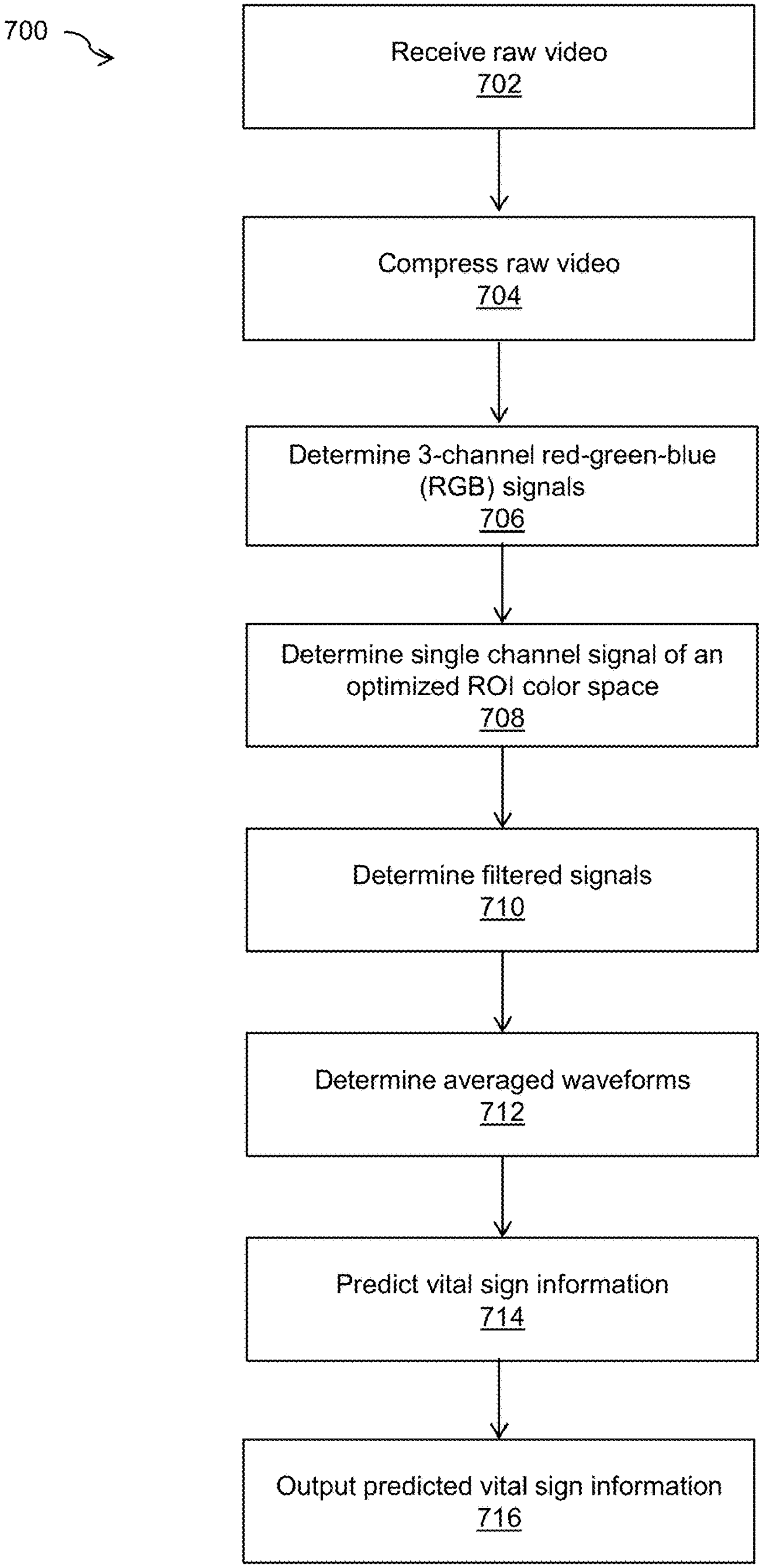
FIG. 7 is a flowchart for a method for contactless predictions of vital signs from raw videos, in accordance with another embodiment.

FIGS. 6 and 7 illustrate another embodiment of a method for contactless predictions of vital signs from raw videos using machine learning models 700 is shown. In this embodiment, a series of ML models are used to generate each vital sign prediction.

At block 702, the input module 110 receives raw video from the camera 103 and/or the storage device 101. Generally, this input raw video will be relatively high-resolution, uncompressed video. At block 704, in some cases, the preprocessing module 112 compresses the raw uncompressed videos to lower resolution videos.

At block 706, the machine learning module 114 determines 3-channel red-green-blue (RGB) signals from an optimized region-of-interest (ROI) mask using a first machine learning model. The ROI mask is used to maximize waveform consistency. The first machine learning model takes the raw video, or compressed video, as input, and outputs 3-channel red-green-blue (RGB) signals from the determined optimal ROIs. The training data can include vital sign locations from a certain ROI. For example, in the case of blood pressure, can include cardiac cycle locations from a cheek ROI.

At block 708, the machine learning module 114 determines, using a second machine learning model, a single channel signal of an optimized ROI color space. The second machine learning model takes as input the 3-channel RGB signals determined from the first machine learning model. The second machine learning model can be trained using the vital sign locations from the certain ROI. For example, in the case of blood pressure, can include cardiac cycle locations from the cheek ROI.

At block 710, the machine learning module 114 determines, using a third machine learning model, filtered signals. The output represents an optimized filter to minimize prediction error. The third machine learning model takes as input the single channel signal determined from the second machine learning model. The third machine learning model can be trained using vital sign ground truth values. For example, blood pressure ground truth values.

At block 712, the machine learning module 114 determines, using a fourth machine learning model, averaged waveforms. The output represents a peak detector to minimize difference from DSP-based cycle locations. The fourth machine learning model takes as input the vital sign locations from the certain ROI. For example, in the case of blood pressure, can include cardiac cycle locations from the cheek ROI.

At block 714, the machine learning module 114 determines, using a fifth machine learning model, predictions for the vital signs. The predicted vital sign can use an optimized DNN to minimize prediction error. The fifth machine learning model takes as input the averaged waveforms. The fifth machine learning model can be trained using ground truth values for the vital sign. For example, in the case of blood pressure, ground truth blood pressure values determined from a sphygmomanometer.

At block 716, the output module 116 outputs the vital sign information predicted by the machine learning module 114 to the output device 102 and/or the storage device 101.

Figure 8:
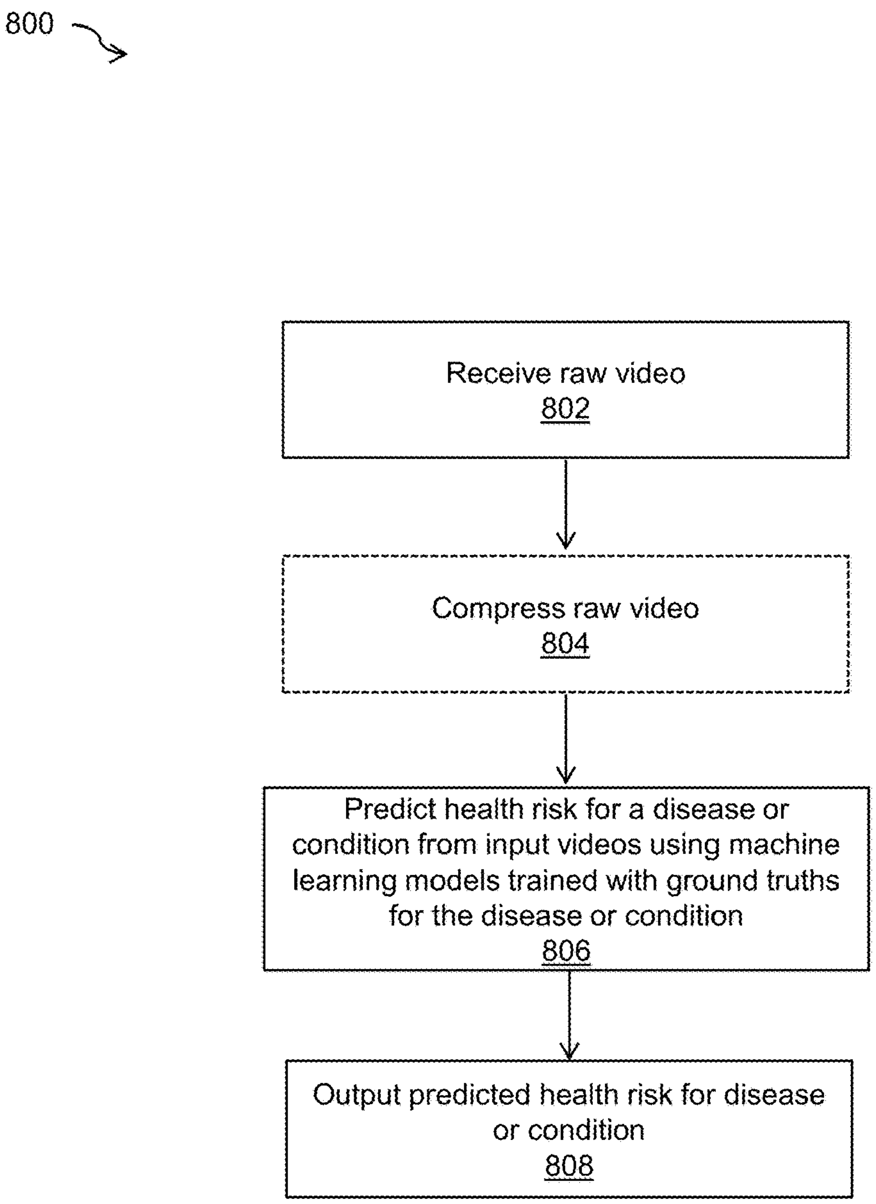
FIG. 8 is a flowchart for a method for contactless predictions of health risk for developing a disease or condition from raw videos using machine learning models, in accordance with another embodiment.

FIG. 8 illustrates an embodiment of a method for contactless predictions of health risk for developing a disease or condition from raw videos using machine learning models 800. The present inventors have conducted example experiments using the present embodiments to predict health risk for developing the diseases or conditions of: fatty liver disease (FLD), hypertension, type-2 diabetes, hypercholesterolemia, and hypertriglyceridemia.

At block 802, the input module 110 receives raw video from the camera 103 and/or the storage device 101. Generally, this input raw video will be relatively high-resolution, uncompressed video.

At block 804, in some cases, the preprocessing module 112 compresses the raw uncompressed videos to lower resolution videos. As described herein, compression enables considerable decrease in video size without any significant loss of information content that might affect accuracy of predictions.

At block 806, the machine learning module 114 feeds the compressed, or in other cases, uncompressed, videos as input to machine learning (ML) models in order to output predicted of health risk factors. In a particular case, the output of the ML models can be between 0 to 1 indicating the risk or likelihood of the person captured in the video having the disease or condition. In some cases, the 0 to 1 output can be converted to a percentage by multiplying by 100.

In some cases, the raw videos can be inputted into the models as 3-dimensional data arrays. The models can be trained using supervised learning, where each input training video has a labeled set of ground truths corresponding to whether or not the person captured in the training video has the disease or condition (for example, whether or not the person captured has FLD). The ground truth data associated with each training video can be provided by medical records and/or medical professionals using diagnostic methods (for example, using imaging methods to detect FLD).

After training, models can be validated for their accuracy and generalizability using a combination of approaches that include k-fold cross validation, performance tuning on separated validation sets, and final performance checks on pristine test sets that represent field data.

The ML models used by the the machine learning module 114 can use any suitable approach. For example, deep learning (DL) models such as convolutional neural networks (CNNs) that is illustrated in the diagram of FIG. 3.

In other cases, a trained ensemble of deep DL models can be used; for example, a primary deep learning model, such as a CNN, and one or more secondary machine learning models, such as Random Forests, XGBoost, Support Vector Machines, or deep neural network (DNN) models. In the ensemble approach, outputs from early convolution layers of the deep learning model (i.e., CNN) are used as input features to the additional machine learning models. Advantageously, the application of machine learning directly on raw videos (or compressed raw videos) bypasses the common need for feature extraction approaches.

Figure 9:
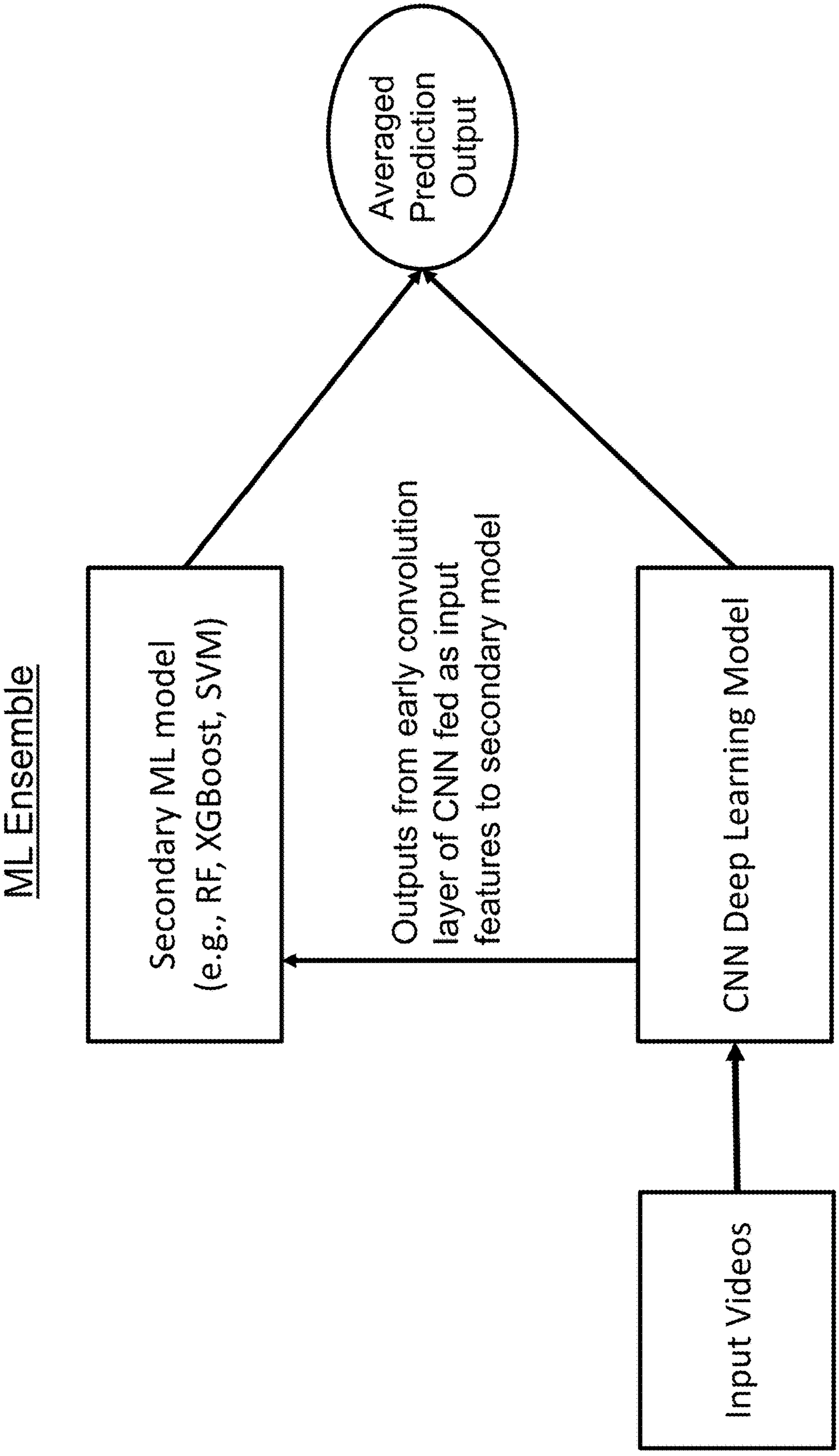
FIG. 9 is a diagram showing an arrangement for a machine learning ensemble, in accordance with the present embodiments.

In an example illustrated in FIG. 9, the input videos can be fed into the primary CNN model and outputs from an early convolution layer of the primary CNN model can be fed as input features to the secondary ML model. The output prediction can be averaged class probability outputs from the primary and secondary models. In a particular case, the averaged output can be between 0 to 1 indicating the risk or likelihood of the person captured in the video having the disease or condition. In some cases, the 0 to 1 output can be converted to a percentage by multiplying by 100.

At block 808, the output module 116 outputs the predicted health risk outputted by the machine learning module 114 to the output device 102 and/or the storage device 101.

In example experiments to verify the embodiments of FIG. 8 for determining health risk for FLD, the present inventors accumulated approximately 5000 videos of training data; each comprising a unique individual with associated ground truth indicating the existence of FLD from medical imaging. Each video spanned approximately 30 seconds. After training of the ML ensemble, the models were tuned further using a validation set (15% of the approximately 5000 videos), and then tested on an untouched, pristine set of participants (a further 15% approximately 5000 videos). Such tuning involved determining hyperparameters; such as, number of trees, depth of trees, filter dimensions, learning rates, activation functions, loss functions, and the like.

In this example experiment, the ML ensemble consisted of a primary CNN model and a secondary XGBoost model. The architecture of the primary CNN model used in the example experiments included, after receiving the raw videos (as 3d arrays) as inputs, (1) a first convolution layer, (2) a first pooling layer, (3) a second convolution layer, (4) a second pooling layer, (5) a third convolution layer, (6) a third pooling layer, and (7) a fully connected layer that outputted a primary prediction as a probability from 0 to 1. This probability indicative of whether the person captured in the input videos has FLD. The secondary XGBoost model used in the example experiments was trained on approximately 500 input features obtained from the second pooling layer of the primary CNN model. The secondary XGBoost model outputted a secondary prediction as a probability from 0 to 1 indicative of whether the person captured in the input videos has FLD. The outputted predictions from the primary CNN model and the secondary XGBoost model were averaged to obtain an output prediction; which was converted to a percentage.

The example experiments evaluated the performance of the machine learning module 114 on the pristine set using the following metrics:

- Confusion Matrix showing Sensitivity and Specificity:
  - Sensitivity (True Positive Rate): The probability of the machine learning module 114 correctly identifying a person who truly has FLD, as having FLD.
  - Specificity (True Negative Rate): The probability of the machine learning module 114 correctly identifying a person who truly does not have FLD, as not having FLD.
- AUC-ROC metric: a measure of the ability of the models to distinguish between classes (i.e. FLD and non-FLD) between 0 and 1; which may be converted into a percentage from 0 to 100.
  - AUC=1 indicates a perfect model ensemble that can correctly predict people with FLD and without FLD.
  - AUC=0 indicates a model ensemble that erroneously predicts all people as having FLD, including those without FLD
  - AUC=0.5 indicates a model ensemble that predicts at chance
  - AUC=0.8 indicates a model ensemble that performs extremely well The example experiments tested the performance of the machine learning module 114 by testing results on approximately 750 unique individuals with scanned videos and corresponding labelled FLD ground truth (i.e. 15% of the training set). The test set of 750 people had approximately 50% with FLD and 50% without FLD. The example experiments determined that the approach of method 800 had a Sensitivity of 85.2%; Specificity of 81.7%, and AUC-ROC=82.2%. Thus, indicating that the method performed extremely well in predicting whether or not the captured subject had FLD.

Figure 10:
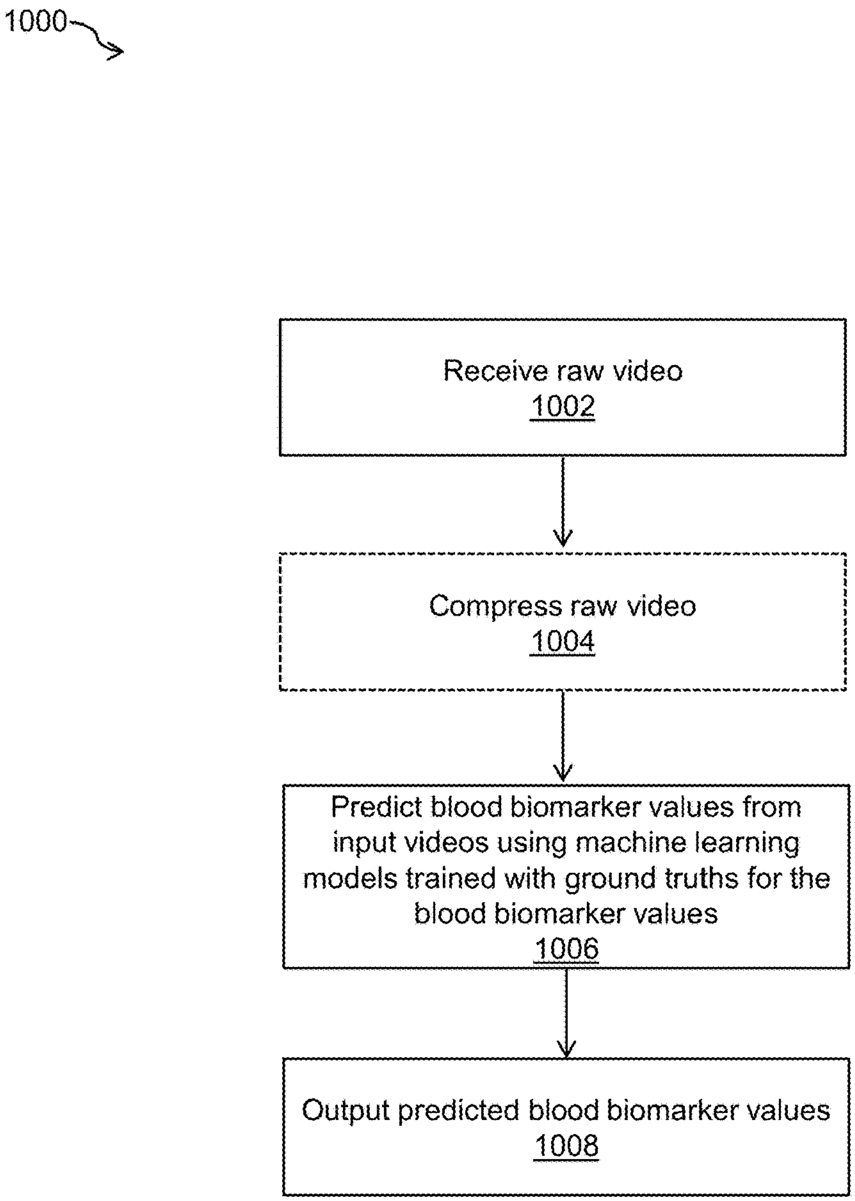
FIG. 10 is a flowchart for a method for contactless predictions of blood biomarker values from raw videos using machine learning models, in accordance with another embodiment.

FIG. 10 illustrates an embodiment of a method for contactless predictions of blood biomarker values from raw videos using machine learning models 1000. The present inventors have conducted example experiments using the present embodiments to predict blood biomarker values of HbA1c and fasting blood glucose.

At block 1002, the input module 110 receives raw video from the camera 103 and/or the storage device 101. Generally, this input raw video will be relatively high-resolution, uncompressed video.

At block 1004, in some cases, the preprocessing module 112 compresses the raw uncompressed videos to lower resolution videos.

At block 1006, the machine learning module 114 feeds the compressed, or in other cases, uncompressed, videos as input to machine learning (ML) models in order to output predicted blood biomarker values. In some cases, the predicted blood biomarker values can be predictions of such blood biomarker being within two or more predetermined ranges. For example, whether the HbA1c value is less than 5.7%, between 5.7% to 6.4%, or greater than 6.4%.

In some cases, the raw videos can be inputted into the models as 3-dimensional data arrays. The models can be trained using supervised learning, where each input training video has a labeled set of ground truths corresponding to the blood biomarker values during the capturing of said video. The ground truth data associated with each training video can be provided by medical records and/or medical professionals using diagnostic methods (for example, using phlebotomy or invasive sensors).

After training, models can be validated for their accuracy and generalizability using a combination of approaches that include k-fold cross validation, performance tuning on separated validation sets, and final performance checks on pristine test sets that represent field data.

The ML models used by the the machine learning module 114 can use any suitable approach. For example, deep learning (DL) models such as convolutional neural networks (CNNs) that is illustrated in the diagram of FIG. 3.

In other cases, a trained ensemble of deep DL models can be used; for example, a primary deep learning model, such as a CNN, and one or more secondary machine learning models, such as Random Forests, XGBoost, Support Vector Machines, or deep neural network (DNN) models. In the ensemble approach, outputs from early convolution layers of the deep learning model (i.e., CNN) are used as input features to the additional machine learning models. Advantageously, the application of machine learning directly on raw videos (or compressed raw videos) bypasses the common need for feature extraction approaches.

At block 1008, the output module 116 outputs the predicted blood biomarker values outputted by the machine learning module 114 to the output device 102 and/or the storage device 101.

Figure 11:
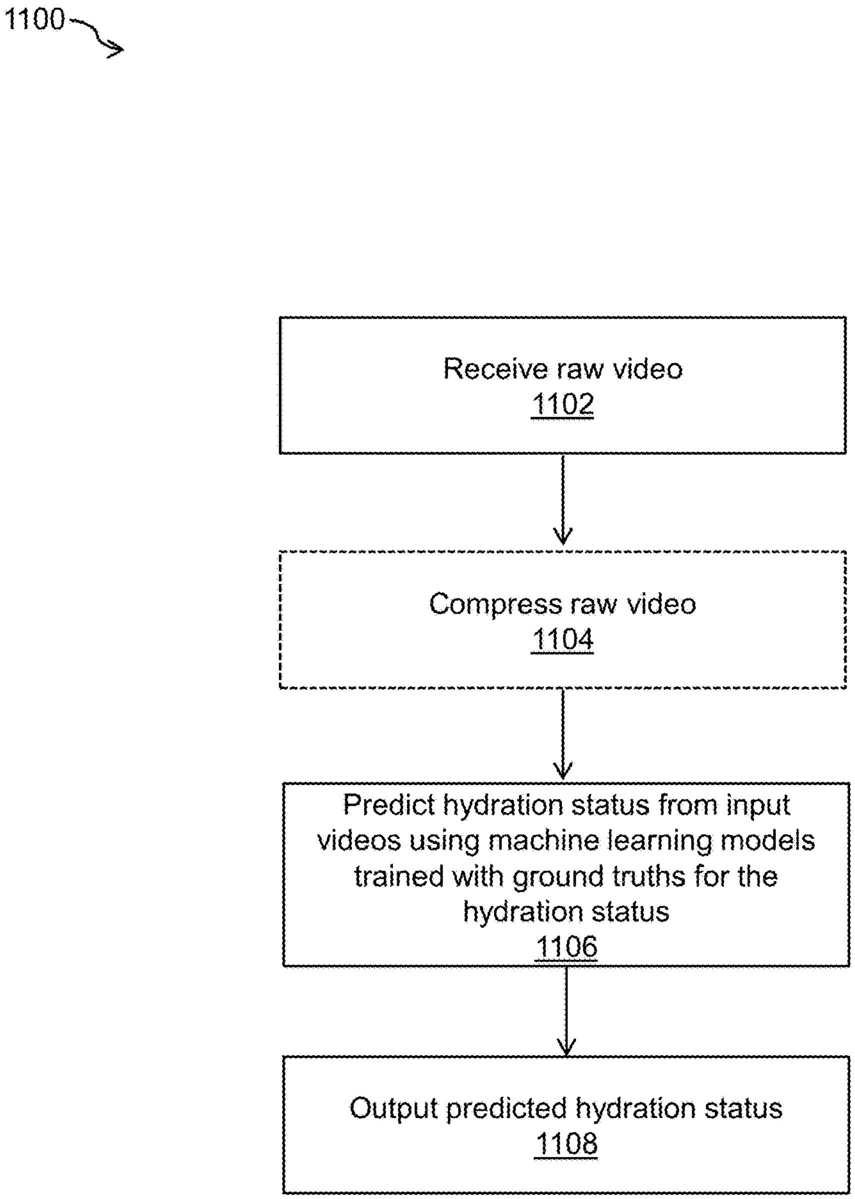
FIG. 11 is a flowchart for a method for contactless predictions of hydration status from raw videos using machine learning models, in accordance with another embodiment.

FIG. 11 illustrates an embodiment of a method for contactless predictions of hydration status from raw videos using machine learning models 1100. The present inventors have conducted example experiments using the present embodiments to predict whether the captured person is dehydrated by predicting hydration status. Generally, dehydration occurs due to water loss that is greater than a given rate, and the water loss is not being replaced. This may happen because of various reasons; such as fever, diarrhea, excessive sweating, being on diuretic pills, or the like. Mild and moderate dehydration is often accompanied with symptoms such as thirst or headache. While mild or moderate dehydration is generally safe, if the symptoms are ignored repeatedly for prolonged periods and water loss is not replenished, this could lead to more serious complications.

At block 1102, the input module 110 receives raw video from the camera 103 and/or the storage device 101. Generally, this input raw video will be relatively high-resolution, uncompressed video.

At block 1104, in some cases, the preprocessing module 112 compresses the raw uncompressed videos to lower resolution videos.

At block 1106, the machine learning module 114 feeds the compressed, or in other cases, uncompressed, videos as input to machine learning (ML) models in order to output predicted hydration status.

In some cases, the raw videos can be inputted into the models as 3-dimensional data arrays. The models can be trained using supervised learning, where each input training video has a labeled set of ground truths corresponding to the hydration status during the capturing of said video. The ground truth data associated with each training video can be provided by medical records and/or medical professionals using diagnostic methods (for example, using phlebotomy or invasive sensors).

After training, models can be validated for their accuracy and generalizability using a combination of approaches that include k-fold cross validation, performance tuning on separated validation sets, and final performance checks on pristine test sets that represent field data.

The ML models used by the the machine learning module 114 can use any suitable approach. For example, deep learning (DL) models such as convolutional neural networks (CNNs) that is illustrated in the diagram of FIG. 3.

In other cases, a trained ensemble of deep DL models can be used; for example, a primary deep learning model, such as a CNN, and one or more secondary machine learning models, such as Random Forests, XGBoost, Support Vector Machines, or deep neural network (DNN) models. In the ensemble approach, outputs from early convolution layers of the deep learning model (i.e., CNN) are used as input features to the additional machine learning models. Advantageously, the application of machine learning directly on raw videos (or compressed raw videos) bypasses the common need for feature extraction approaches.

The hydration status being outputted from the fully connected layer can be adapted into a class probability ranging from 0 to 1, where the higher the probability, the higher the likelihood of a person being dehydrated. This probability may be expressed as a percentage. Typically, a percentage likelihood of over 50% suggests that the user is dehydrated.

Various parameters and hyperparameters are determined during the training phase of the model. Parameters and hyperparameters can include, for example, number and size of filters, type of padding used, choice of activation functions and learning rates, pooling strategy, choice of cost function, batch sizes and number of epochs for determining early stopping, choice of using dropout, and the like.

At block 1108, the output module 116 outputs the predicted hydration status outputted by the machine learning module 114 to the output device 102 and/or the storage device 101.

In further cases, the system 100 can be used to predicting multiyear (for example, 10-year) cardiovascular disease (CVD) risks. Atherosclerotic cardiovascular disease or cardiovascular disease involves diseases of the heart and blood vessels. Heart attack and stroke are typically the first acute signs of CVD. They occur due to blockages from fatty deposit build-up on the inner walls of blood vessels supplying blood to the brain or the heart. The risk of having CVD can be defined as the risk of having a heart attack, stroke, or coronary heart disease. It generally applies to people who have not already had a heart attack or stroke. Given that CVD is a leading cause of death and disability, routine estimation of CVD risk can encourage healthy lifestyle changes; thus mitigating risk factors associated with CVD.

One particular approach for estimating a person's CVD risk of experiencing a heart attack, stroke, or death due to coronary heart disease is a Pooled Cohort Equation (PCE). This approach predicts the likelihood of such an event happening within the next 10 years. PCE estimates CVD risk using demographic information (e.g., age, sex at birth), systolic blood pressure, smoking status, diabetes status, cholesterol levels, and race. There are at least two significant drawbacks of using this approach. First, PCE relies on invasive blood tests for obtaining cholesterol information. Second, it relies on Cox proportional hazards-based regression, which is a conventional statistical technique, unlike more sophisticated data-driven approaches.

Embodiments of the system 100 can advantageously overcome the drawbacks of PCE. Particularly, using data-driven machine learning approaches to provide multiyear CVD risk assessments. These assessments can be determined for shorter and/or longer time durations than only 10 years (e.g., 1 year to 20 years). These assessments advantageously do not require invasive blood tests. Embodiments of the system 100 can be used to predict the risk or likelihood of someone having a CVD event for each year in the next 'n' years, using, for example, 'n' separate machine learning based classifiers. For example, prediction of the CVD risks for each of the next 15 years (n=15), there can be 15 separate machine learning models; each representing the risk for Year 1, Year 2, Year 3, and so on, until Year 15. In some cases, the machine learning model does not require information about race or cholesterol levels like the PCE; rather, the model can use demographic information (for example, age, sex at birth, height, and weight), systolic blood pressure, diastolic blood pressure, smoking status, and/or diabetes status as input features.

Figure 12:
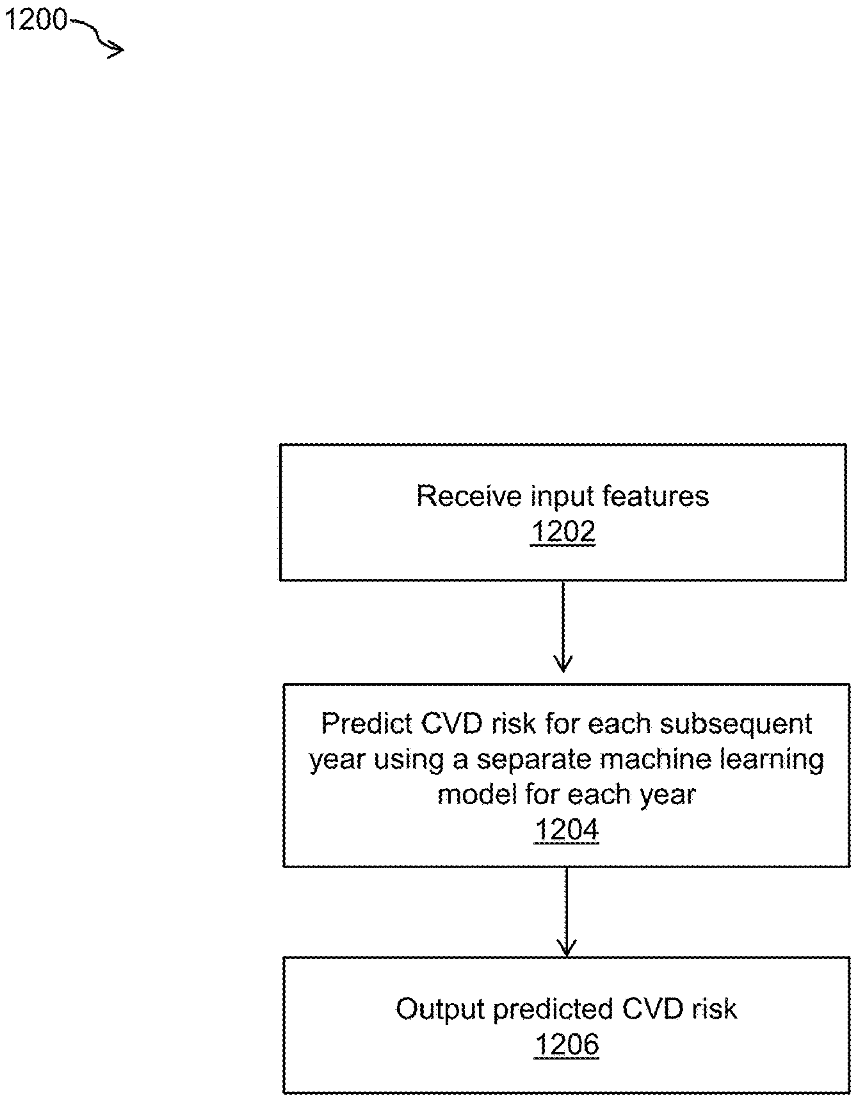
FIG. 12 is a flowchart for a method for predicting multiyear cardiovascular disease risks using machine learning models, in accordance with another embodiment.

FIG. 12 illustrates an embodiment of a method for predicting multiyear cardiovascular disease risks using machine learning models 1200.

At block 1202, the input module 110 receives input features from the storage device 101 comprising demographic information, systolic blood pressure, and diastolic blood pressure. In some cases, smoking status, and/or diabetes status can also be received as input features.

At block 1204, the machine learning module 114 feeds the input features as input to machine learning (ML) models in order to output predicted CVD risk.

In these embodiments, the ML model or ML ensemble could use a single ML model or a combination of ML models (such as that illustrated in FIG. 4). ML models used can include, for example, a multilayer perceptron (MLP), support vector machines, or tree-based and gradient boosting models (such as Random Forests or XGBoost). The architecture used for the ML model and/or ensemble can depend on the type of non-linear function used for predicting the CVD risk; thereby demanding varying levels of complexity in the model's architecture that need to be determined during training. In general, there will be similarities in the model architecture used for each of the 'n' models corresponding to the CVD risk for 'n' successive years.

Detecting and predicting the risk of having CVD can be treated as a binary classification problem; either the person falls into a class indicating a CVD event, or the person falls into a class indicating no CVD event. The ML models can be trained on numerous samples (for example, thousands of samples) using supervised learning; where each sample has a labeled ground truth indicating whether the person was diagnosed with a CVD event or not for a given year. The training data can include historical data for 'n' successive years indicating whether there were CVD events for the given year; and, in most cases, with no CVD events occurring prior to the first sample year. After training, models can be validated for their accuracy and generalizability using a combination of approaches that include, for example, k-fold cross validation, performance tuning on separated validation sets, and final performance checks on pristine test sets that represent field data.

Outputs from the final layer of each model can be adapted into a class probability ranging from 0 to 1; where the higher the probability, the higher the likelihood of a person having a CVD event for that particular year. In some cases, this probability can be expressed as a percentage; for example, a percentage likelihood of greater than 50% indicates a CVD risk. Parameters and hyperparameters determined during training can include, for example, the number of hidden layers, the dimensionality of each hidden layer, activation function and learning rate selection, cost function selection, batch sizes and number of epochs for determination of early stoppage, whether to use dropout, and the like.

In some cases, where the output is expressed as a probability, the probability outputs from each of the 'n' years can be smoothed to predict a steady increase in CVD risk over 'n' years; which is reflective of how a person's risk would increase from the first year to the $n^{th}$ year.

In some cases, raw videos may be used as input to the trained ML model or ensemble. When the trained ML model generates CVD risk predictions on unseen input data, the system can make blood pressure predictions (i.e. systolic blood pressure and diastolic blood pressure) as described herein. These predicted values from raw videos would then be used as input features to the multiyear CVD risk models, in the absence of external systolic and diastolic blood pressure measurements.

At block 1206, the output module 116 outputs the predicted hydration status outputted by the machine learning module 114 to the output device 102 and/or the storage device 101.

The present inventors conducted example experiments using the present embodiments to predict multiyear CVD risk. In these example experiments, 'n' was equal to 20 years.

In the example experiments, the training dataset comprised approximately 30,000 unique individuals from the United States, over a 20-year period, with ground truth indicating whether they previously had a heart attack or stroke. Data collection started at baseline and continued for 20 years. After training, all ML models were tuned further to a validation set (15%), and then tested on an untouched, pristine set of input from other participants (15%). Tuning involved making hyperparameter choices; number of trees, depth of trees, filter dimensions, learning rates, activation functions, loss functions, and the like.

In the example experiments, the architecture of the ML models was XGBoost; however, it is understood that any suitable model could have been used, such as, SVM, RF, DNN, or the like. There were twenty separate models; one for each successive year. The models were trained on demographic information, systolic blood pressure, diastolic blood pressure, smoking status, and diabetes status. The prediction output for each model was a probability from 0 to 1, representative of the probability of having CVD risk; and was expressed as a percentage.

In the example experiments, performance of the ML ensemble on the pristine set was captured using the following metrics:

- Confusion Matrix showing sensitivity and specificity. Sensitivity (True Positive Rate) was the probability of the ML ensemble correctly identifying a person who truly has a CVD event, as having CVD. Specificity (True Negative Rate) was the probability of the ML ensemble correctly identifying a person who truly does not have a CVD event, as not having CVD.
- AUC-ROC metric, which is a measure of the ability of a classifier to distinguish between classes (i.e., CVD and non-CVD) between 0 and 1. This may be converted into a percentage from 0 to 100. AUC=1 indicates a perfect classifier that can correctly predict people with CVD and without CVD. AUC=0 indicates a classifier that erroneously predicts all people as having CVD, including those without CVD. AUC=0.5 indicates a classifier that predicts at chance and AUC=0.8 indicates a classifier that performs extremely well.

The example experiments completed performance testing results on approximately unique individuals with corresponding labelled CVD ground truth. The test set of 750 people, for each year from 1 to 20, would have approximately 50% with CVD and 50% without CVD. The performance testing for sensitivity, specificity, and AUC-ROC for exemplary one of the 20 years was sensitivity=84.1%, specificity=81.6%, and AUC-ROC=81.4%. Indicative of the substantial performance of the present embodiments, the determined AUC-ROC metric was:

Year 1=80.2%;
Year 2=81.4%;
Year 3=82.3%;
Year 4=80.7%
. . .
Year 20=83.5%

In further embodiments, the system 100 can be used to predict CVD risk in a specific timeframe into the future (e.g., at 10 years from measurement) from raw video without requiring inputs of cholesterol, diabetes, and blood pressure information. Such approach provides a significant advantage over the PCE, which requires blood tests and measurement of blood pressure. Advantageously, this approach does not require any expert-driven manual signal processing or feature engineering.

Figure 13:
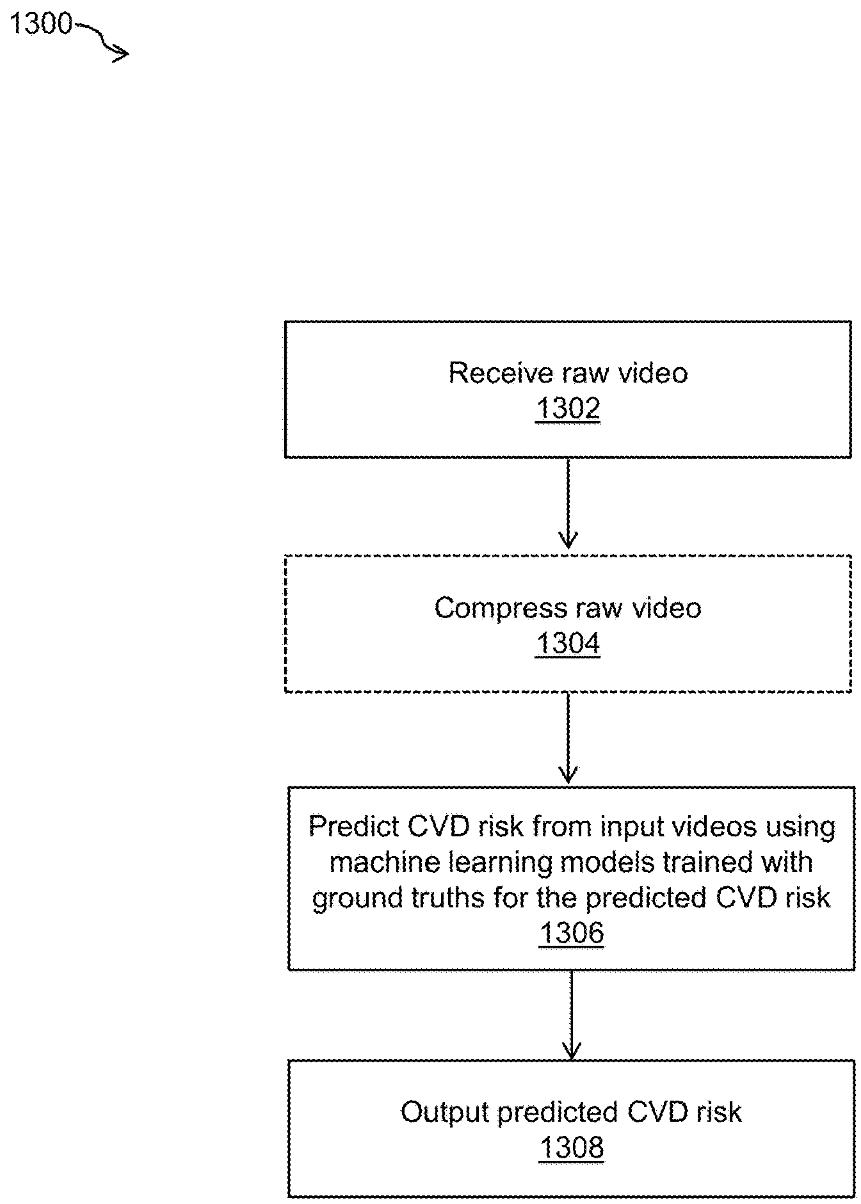
FIG. 13 is a flowchart for a method for predicting cardiovascular disease risk from raw videos using machine learning models, in accordance with another embodiment.

FIG. 13 illustrates an embodiment of a method for predicting CVD risk from raw videos using machine learning models 1300.

At block 1302, the input module 110 receives raw video from the camera 103 and/or the storage device 101. Generally, this input raw video will be relatively high-resolution, uncompressed video.

Each raw uncompressed video can be collected for a specific duration, at a specific sampling rate, and may be visualized as a series of two-dimensional frames in time; with each frame having a given fixed height and fixed width. In an example, each video can be 30 seconds long and collected at a sampling rate of 30 frames per second (fps), resulting in a total of 900 frames. Each frame can be an image at a particular point in time, with a bit depth of 8 bits, consisting of red, green, and blue (R,G,B) color channels. Each frame can have a height of 1280 pixels and a width of 720 pixels. In this example, each raw video has an approximate size of 2.3 GB.

At block 1304, in some cases, the preprocessing module 112 compresses the raw uncompressed videos to lower resolution videos. Compression enables for a considerable decrease in video size without any significant loss of information content that might affect the accuracy of the prediction. The reduced video size can improve speed and ease of processing by saving memory resources. Additionally, converting the video from high to low resolution can provide for anonymization of the identity of the person in the video; thus, addressing various privacy concerns.

In the above example, each such video can be converted to a low resolution compressed video by decreasing the height and width of each individual frame. In this way, each video can still consist of 900 frames, with each frame still consisting of RGB channels. However, bit depth is increased to 12 bits, height is reduced to 32 pixels, and width is reduced to 16 pixels. This results in each video having a reduced size of approximately 2.0 MB from the original size of 2.3 GB, without apparent loss in information content required for making predictions in the present embodiment.

At block 1306, the machine learning module 114 feeds the compressed, or in other cases, uncompressed, videos as input to machine learning (ML) model(s) in order to output predicted CVD risk.

The ML model can include a single ML model or ensemble of models. The ML model can include individual deep learning (DL) models, for example, convolutional neural networks (CNNs). In other cases, the ML ensemble can include a combination of DL models, including CNNs and deep neural networks (DNNs), for example, multi-layer perceptrons (MLPs). In other cases, the ensemble can include a combination of DL models and other ML models, for example, Support Vector Machines, tree-based models and gradient boosting models (such as Random Forests, XGBoost). Any suitable architecture of the ML model and/or ensemble can be used depending on the type of non-linear function required for predicting the CVD risk, thereby demanding varying levels of complexity in the model's architecture that need to be determined during training.

The problem of detecting and predicting the risk of having CVD in a given time period (e.g., 10-years) can be treated as a binary classification problem; either the person falls into a class indicating a CVD event, or the person falls into a class indicating no CVD event. The ML model or ensemble can be trained using supervised learning, where each input training video has a labeled ground truth indicating whether the person was diagnosed with a CVD event or not, for example, based on the CVD risk prediction from the Pooled Cohort Equation (PCE). In such example, the PCE prediction serves as the ground truth for the ML model ensemble. Models can be trained using any suitable number of training videos; for example, on thousands of labelled training videos. While the PCE does not use the videos themselves to generate the prediction, it uses corresponding inputs from the captured individuals; such as demographics (i.e. age, sex at birth), systolic blood pressure, diabetes status, and cholesterol levels, in order to make its predictions that serve as ground truth in the present embodiment.

After training, the ML models can be validated for their accuracy and generalizability using a combination of approaches that include, for example, k-fold cross validation, performance tuning on separated validation sets, and final performance checks on pristine test sets that represent field data.

In some cases, where a CNN model is used, as illustrated in FIG. 3, the CNN model can be a three-dimensional model that receives raw compressed video input in the form of three dimensional data arrays consisting of pixel values. The CNN architecture can include of a series of convolution and pooling layers followed by a fully connected layer. The convolution layer automatically extracts relevant features from each image frame of the video using several kernels (filters). The number of features extracted will generally depend on the number of filters used by the CNN. The pooling layer enables selection of the most salient features while also reducing feature dimensionality. Several of these convolution and pooling layers can be used in sequence within a CNN's architecture before finally providing these outputs to a fully connected layer as a flattened vector. The series of convolution layers provide an automated feature extraction hierarchy. For instance, early convolution layers in the CNN represent extraction of finer grained or lower-level features while convolution layers occurring later represent coarser or higher-level features. Outputs from the fully connected layer can be adapted into a class probability ranging from 0 to 1, where the higher the probability, the higher the likelihood of a person having CVD risk. In some cases, this probability may be expressed as a percentage. Typically, a percentage likelihood of over 50% suggests that the user has CVD risk. Various parameters and hyperparameters can be determined during the training phase of the CNN model and can include a number of number and size of filters, a type of padding used, a choice of activation functions and learning rates, a pooling strategy, a choice of cost function, batch sizes and number of epochs for determining early stopping, a choice of using dropout, amongst others.

In some cases, depending on how complex the non-linear solution needs to be for CVD risk prediction, an ensemble ML model can be used; such as illustrated in FIG. 4. The ensemble can be used to improve the accuracy of predictions. In an example, the ensemble can consist of at least two models: a CNN model and a DNN model. A support vector machine (SVM), or a tree-based or gradient boosting model (such as Random Forests or XGBoost) may also be used in place of a DNN. The DNN (or MLP) model generally can consist of an input layer and a series of hidden layers followed by an output layer. The DNN model uses features extracted by the early convolution layers of the CNN as inputs to its network. Hyperparameters, for example, a number of input features, a number of hidden layers, a dimensionality of each hidden layer, activation functions used, early stopping criteria, and a choice of using dropout, amongst others, can be determined during the training phase. The ML ensemble determines the weight of each model's contribution. Depending on the number and types of individual ML models used (e.g. CNN, DNN etc.), and their accuracy in making predictions on a validation set, contribution weights for each model are tuned using other ML techniques such as linear regression with regularization. The ML ensemble can determine the weight of each model's contribution depending on the number and types of individual ML models used (e.g. CNN, DNN etc.) and their accuracy in making predictions on a validation set. Contribution weights for each model can be tuned using any suitable technique, such as linear regression with regularization.

At block 1308, the output module 116 outputs the predicted risk for a CVD event, as outputted by the machine learning module 114, to the output device 102 and/or the storage device 101.

The present inventors conducted example experiments using the present embodiments to predict CVD risk from raw videos. In these example experiments, the prediction period was for 10 years.

In the example experiments, the raw videos received as input comprised uncompressed 30 second videos at 30 fps; thus, 900 frames×3 channels×1280 height×720 width. Meaning the input videos were 8 bits and totalled 2.3 GB. The uncompressed video was converted to a low resolution compressed video: 900 frames×3 channels×32 height×16 width. Meaning the compressed videos were 12 bits and totalled 2.0 MB. The compressed videos were provided as input to machine learning models as 3-dimensional data arrays. The ML models were trained with labeled ground truth information on CVD risk for a 10-year period (as predicted by the PCE). The predictions were outputted by the ML models as class probabilities.

In the example experiments, the training dataset consisted of approximately 30,000 unique individuals with 30-second raw videos, demographic information, and blood work data showing diabetes status and cholesterol information. This data was fed to the PCE to compute 10-year CVD risk for each individual. These calculated PCE risks were used as the ground truths for the ML models. After training, the ML models were tuned further to a validation set (15%), and then tested on an untouched, pristine set of participants (15%). Tuning involved making hyperparameter choices; number of trees, depth of trees, filter dimensions, learning rates, activation functions, loss functions, and the like.

In the example experiments, the ML architecture consisted of an ML ensemble comprising a CNN model and an XGBoost model. The CNN architecture included:

Raw videos (3-d arrays) received as inputs;
Convolution;
Pooling;
Convolution;
Pooling;
Convolution;
Pooling;
Fully Connected Layer; and
Prediction Output as a probability from 0 to 1 that was representative of having CVD risk within 10 years.

The XGBoost model was trained on approximately 500 input features obtained from the 2nd pooling layer of the CNN. The XGBoost prediction output was a probability from 0 to 1 that was representative of having CVD risk within 10 years.

In the example experiments, the prediction probabilities from the CNN and XGBoost were averaged to obtain a final prediction, which was converted to a percentage.

In the example experiments, performance of the ML ensemble on the pristine set was captured using the following metrics:

Confusion Matrix showing sensitivity and specificity. Sensitivity (True Positive Rate) was the probability of the ML ensemble correctly identifying a person who truly has a CVD event, as having CVD. Specificity (True Negative Rate) was the probability of the ML ensemble correctly identifying a person who truly does not have a CVD event, as not having CVD.

AUC-ROC metric, which is a measure of the ability of a classifier to distinguish between classes (i.e., CVD and non-CVD) between 0 and 1. This may be converted into a percentage from 0 to 100. AUC=1 indicates a perfect classifier that can correctly predict people with CVD and without CVD. AUC=0 indicates a classifier that erroneously predicts all people as having CVD, including those without CVD. AUC=0.5 indicates a classifier that predicts at chance and AUC=0.8 indicates a classifier that performs extremely well.

The example experiments completed performance testing results on approximately unique individuals with corresponding labelled CVD ground truth. The test set of 750 persons included approximately 50% with CVD and 50% without CVD. The performance testing determined a sensitivity of 84.1%, a specificity of 81.6%, and an AUC-ROC of 81.4%. Thus, illustrating the present embodiments substantial ability to predict CVD risk using raw videos as input.

In further embodiments, optical sensors pointing, or directly attached to the skin of any body parts such as for example the wrist or forehead, in the form of a wrist watch, wrist band, hand band, clothing, footwear, glasses or steering wheel may be used. From these body areas, the system 100 may also make the predictions described herein.

In still further embodiments, the system may be installed in robots and their variables (e.g., androids, humanoids) that interact with humans to enable the robots to detect vital signs or conditions on the face or other-body parts of humans whom the robots are interacting with.

The foregoing system and method may be applied to a plurality of fields. In one case, the system may be installed in a smartphone device to allow a user of the smartphone to measure their vital signs, health risks, and/or blood biomarker values. In other cases, the system may be provided in a video camera located in a hospital room to allow the hospital staff to monitor the vital signs of a patient without causing the patient discomfort by having to attach a device to the patient. Other applications may become apparent.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A method for contactless predictions of one of vital signs, health risk for a disease or condition, blood biomarker values, and hydration status, the method executed on one or more processors, the method comprising:

receiving a raw video capturing a human subject;

determining one of vital signs, health risk for a disease or condition, blood biomarker values, and hydration status using a trained machine learning model, the machine learning model taking the raw video as input in the form of three-dimensional data arrays consisting of pixel values, the machine learning model trained using a plurality of training videos where ground truth values for the vital signs, the health risk for a disease or condition, the blood biomarker values, or the hydration status were known during the capturing of the training video, wherein the trained machine learning model comprises an ensemble of machine learning models comprising a primary three-dimensional convolutional neural network and a secondary machine learning model comprising a gradient boosting machine learning model, wherein features extracted by early convolution layers of the primary convolutional neural network are provided as input to the secondary machine learning model, and wherein determining the one of vital signs, health risk for a disease or condition, blood biomarker values, and hydration status comprises averaging a prediction output of the primary convolutional neural network and a prediction output of the secondary machine learning model; and outputting the predicted vital signs, health risk for a disease or condition, blood biomarker values, or hydration status.

2. The method of claim 1, wherein the gradient boosting machine learning model comprises an Extreme Gradient Boosting (XGBoost) model.

3. The method of claim 1, wherein the prediction for the health risk for the disease or condition comprises predicting a risk for cardiovascular disease.

4. The method of claim 3, wherein the machine learning model is trained using labeled ground truth data, the ground truth determined using a pooled cohort equation of cardiovascular disease risk.

5. The method of claim 1, wherein the prediction for health risk for the disease or condition is represented as a percentage likelihood of having the disease or condition in the future.

6. The method of claim 5, wherein the percentage likelihood for having the disease or condition is for a given timeframe in the future.

7. The method of claim 1, wherein the raw video is compressed prior to being taken as input in the machine learning model.

8. A system for contactless predictions of one of vital signs, health risk for a disease or condition, blood biomarker values, and hydration status, the system comprising one or more processors and a data storage, the data storage comprising instructions to execute, on the one or more processors:

an input module to receive a raw video capturing a human subject;

a machine learning module to determine one of vital signs, health risk for a disease or condition, blood biomarker values, and hydration status using a trained machine learning model, the machine learning model taking the raw video as input in the form of three-dimensional data arrays consisting of pixel values, the machine learning model trained using a plurality of training videos where ground truth values for the vital signs, the health risk for a disease or condition, the blood biomarker values, or the hydration status were known during the capturing of the training video, wherein the trained machine learning model comprises an ensemble of machine learning models comprising a primary three-dimensional convolutional neural network and a secondary machine learning model comprising a gradient boosting machine learning model, wherein features extracted by early convolution layers of the primary convolutional neural network are provided as input to the secondary machine learning model, and wherein the machine learning module determines the one of vital signs, health risk for a disease or condition, blood biomarker values, and hydration status by averaging a prediction output of the primary convolutional neural network and a prediction output of the secondary machine learning model; and an output module to output the predicted vital signs, health risk for a disease or condition, blood biomarker values, or hydration status.

9. The system of claim 8, wherein the gradient boosting machine learning model comprises an Extreme Gradient Boosting (XGBoost) model.

10. The system of claim 8, wherein the prediction for the health risk for the disease or condition comprises predicting a risk for cardiovascular disease.

11. The system of claim 10, wherein the machine learning module trains the machine learning model using labeled ground truth data, the ground truth determined using a pooled cohort equation of cardiovascular disease risk.

12. The system of claim 8, wherein the prediction for health risk for the disease or condition is represented as a percentage likelihood of having the disease or condition in the future.

13. The system of claim 12, wherein the percentage likelihood for having the disease or condition is for a given timeframe in the future.

14. The system of claim 8, further comprising a preprocessing module to compress the raw video prior to being taken as input in the machine learning model.

* * * * *